United States Patent [19]

Rephaeli

[11] Patent Number: 5,939,455
[45] Date of Patent: *Aug. 17, 1999

[54] THERAPEUTIC AUGMENTATION OF OXYALKYLENE DIESTERS AND BUTYRIC ACID DERIVATIVES

[75] Inventor: Ada Rephaeli, North Caldwell, N.J.

[73] Assignee: Beacon Laboratories, Inc., Phoenix, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/814,222

[22] Filed: Mar. 11, 1997

[51] Int. Cl.$^6$ .......... A61K 31/225; A61K 31/66; A61K 31/62; A61K 31/40

[52] U.S. Cl. .......... 514/547; 514/117; 514/121; 514/124; 514/161; 514/420; 514/512; 514/533; 514/548; 514/568; 514/569; 514/570

[58] Field of Search .......... 514/547, 512, 514/533, 548, 568, 569, 570, 420, 161, 117, 121, 124

[56] References Cited

U.S. PATENT DOCUMENTS

| | | | |
|---|---|---|---|
| 2,940,855 | 6/1960 | Beavers et al. | 430/543 |
| 3,219,630 | 11/1965 | Sidi | 525/419 |
| 3,293,220 | 12/1966 | Minami et al. | 525/400 |
| 3,336,262 | 8/1967 | Sidi | 528/230 |
| 3,578,671 | 5/1971 | Brown | 548/236 |
| 3,700,722 | 10/1972 | McTeer | 560/224 |
| 3,720,706 | 3/1973 | Lapporte et al. | 560/238 |
| 3,752,844 | 8/1973 | Pfister et al. | 560/10 |
| 3,812,176 | 5/1974 | Lapporte et al. | 560/238 |
| 3,931,412 | 1/1976 | Kensler, Jr. et al. | 514/547 |
| 4,012,526 | 3/1977 | Kensler, Jr. et al. | 514/547 |
| 4,105,681 | 8/1978 | Bollag et al. | 544/111 |
| 4,123,552 | 10/1978 | Kensler, Jr. et al. | 514/547 |
| 4,150,137 | 4/1979 | Noda et al. | 514/345 |
| 4,198,416 | 4/1980 | Koeda et al. | 514/350 |
| 4,215,215 | 7/1980 | Bollag et al. | 544/176 |
| 4,442,124 | 4/1984 | Niklaus | 514/547 |
| 4,479,963 | 10/1984 | Gruenfeld | 514/212 |
| 4,541,944 | 9/1985 | Sanderson | 510/371 |
| 4,545,784 | 10/1985 | Sanderson | 8/107 |
| 4,613,505 | 9/1986 | Mizushima et al. | 514/461 |
| 4,699,925 | 10/1987 | Uchida et al. | 514/559 |
| 4,760,057 | 7/1988 | Alexander | 514/187 |
| 4,816,570 | 3/1989 | Farquhar | 536/26.8 |
| 4,885,311 | 12/1989 | Parish et al. | 514/549 |
| 4,900,478 | 2/1990 | Gross | 554/170 |
| 4,916,230 | 4/1990 | Alexander | 546/318 |
| 4,927,966 | 5/1990 | Kalmen | 562/594 |
| 5,025,029 | 6/1991 | Perrine | 514/381 |
| 5,030,654 | 7/1991 | Barnish et al. | 514/510 |
| 5,158,773 | 10/1992 | Gross | 514/529 |
| 5,162,573 | 11/1992 | Chiesi et al. | 560/224 |
| 5,185,436 | 2/1993 | Villa et al. | 536/4.1 |
| 5,196,567 | 3/1993 | Uchida et al. | 560/102 |
| 5,200,553 | 4/1993 | Nudelman et al. | 560/263 |
| 5,216,004 | 6/1993 | Perrine | 514/381 |
| 5,412,137 | 5/1995 | Prashad et al. | 558/146 |
| 5,569,675 | 10/1996 | Rephaeli et al. | 514/547 |
| 5,661,179 | 8/1997 | Samid | 514/538 |
| 5,679,638 | 10/1997 | Teicher | 514/6 |
| 5,710,176 | 1/1998 | Rephaeli et al. | 514/548 |

FOREIGN PATENT DOCUMENTS

| | | |
|---|---|---|
| 890221 | 1/1982 | Belgium . |
| 0 056 189 A1 | 7/1982 | European Pat. Off. . |
| 79872 A1 | 5/1983 | European Pat. Off. . |
| 132 814 A1 | 2/1985 | European Pat. Off. . |
| 144 845 A1 | 6/1985 | European Pat. Off. . |
| 250 967 A2 | 1/1988 | European Pat. Off. . |
| 0319316 A2 | 6/1989 | European Pat. Off. . |
| 0 371 789 A2 | 6/1990 | European Pat. Off. . |
| 1 386 096 | of 1965 | France . |
| 1 540 418 | 9/1968 | France . |
| 2638457 | 4/1990 | France . |
| 26 25 688 A1 | 12/1977 | Germany . |
| 54-90174 | 7/1979 | Japan . |
| 58-15912 | 1/1983 | Japan . |
| 60-016923 | 1/1985 | Japan . |
| 63-101348 | 5/1988 | Japan . |
| 1-128872 | 5/1989 | Japan . |
| WO94/01415 | 1/1994 | Japan . |
| 635 062 | 3/1983 | Switzerland . |
| 1177442 | 1/1970 | United Kingdom . |
| 1 220 442 | 1/1971 | United Kingdom . |
| 1 220 447 | 1/1971 | United Kingdom . |
| 1 345 628 | 1/1974 | United Kingdom . |
| 1 382 010 | 1/1975 | United Kingdom . |
| 2126082 | 3/1984 | United Kingdom . |
| WO92/14706 | 9/1992 | WIPO . |
| WO93/19778 | of 1993 | WIPO . |
| WO93/07866 | 4/1993 | WIPO . |
| WO95/10271 | 4/1995 | WIPO . |
| WO98/00127 A1 | 1/1998 | WIPO . |

OTHER PUBLICATIONS

Bednarski, et al., "Rabbit Muscle Aldolase as a Catalyst in Organic Synthesis", Chem. Abstracts, vol. 110, Abstract 57935c, 1989.

Bhatia, et al., "Induction of Cell Differentiation Potentiates Apoptosis Triggered by Prior Exposure to DNA–damaging Drugs", Cell Growth and Differentiation, vol. 6, pp. 937–944, 1995.

Boffa, et al., "Manifold Effects of Sodium Butyrate on Nuclear Function", J. Biol. Chem., vol. 256, No. 18, pp. 9612–9621, 1981.

Bourgeade, et al., "Reorganization of the Cytoskeleton by Interferon in MSV–Transformed Cells", J. of Interferon Res., vol. 1, No. 2, pp. 323–332, 1981.

(List continued on next page.)

Primary Examiner—Kevin E. Weddington
Attorney, Agent, or Firm—Kenyon & Kenyon

[57] ABSTRACT

This invention provides a method of augmenting the therapeutic activity of an oxyalkylene-containing compound, butyric acid, a butyric acid salt or butyric acid derivative by administering an inhibitor of β-oxidation of fatty acids to a patient or to host cells. Pharmaceutical compositions are also included.

63 Claims, No Drawings

OTHER PUBLICATIONS

Brant and Conklin, "Acrolein Diacylates", Chem. Abstracts, vol. 40, p. 3127, 1946.

Carstea, et al., "Analogues of Butyric Acid that Increase the Expression of Transfected DNAs", Biochem. Biophys. Res. Com., vol. 192, No. 2, pp. 649–656, 1993.

Cheng, et al., "Functional Activation of the Cystic Fibrosis Trafficking Mutant deltaF508–CFTR by Overexpression", American Journal of Physiology, vol. 268, No. 4, pp. L615–L624, 1995.

Christl, et al., "Antagonistic Effects of Sulfide and Butyrate on Proliferation of Colonic Mucosa, A Potential Role for These Agents in the Pathogenesis of Ulcerative Colitis", Digestive Diseases and Sciences, vol. 41, No. 12, pp. 2477–2481, 1996.

Conway, et al., "Induction of Apoptosis by Sodium Butyrate in the Human Y–79 Retinoblastoma Cell Line", Oncology Research, vol. 7, No. 6, pp. 289–297, 1995.

de Haan, et al., "Effects of Sodium Butyrate on the Synthesis and Methylation of DNA in Normal Cells and Their Transformed Counterparts", Cancer Res., vol. 46, No. 2, pp. 713–716, 1986.

Deschamps, et al., "Inhibition by Salicylic Acid of the Activation and thus Oxidation of Long Chain Fatty Acids. Possible Role in the Development of Reye's Syndrome", Journal of Pharmacology and Experimental Therapeutics, vol. 259, No. 2, pp. 894–904, 1991.

Falch and Krogsgaard–Larsen, "Esters of Isoguvacine as Potential Prodrugs", J. Med. Chem., vol. 24, pp. 285–289, 1981.

Farquhar, et al., "Biologically Reversible Phosphate Protective Groups", J. Pharm. Sci., vol. 72, No. 3, pp. 324–325, 1983.

Farquhar, et al., "Synthesis and Antitumor Evaluation of Bis[(pivaloyloxy)methyl] 2'–Deoxy–5–fluorouridine 5'–Monophosphate (FdUMP): A Strategy to Introduce Nucleotides into Cells", J. Med. Chem., vol. 37, No. 23, pp. 3902–39009, 1994.

Freneaux, et al., "Inhibition of the Mitochondrial Oxidation of Fatty Acids by Tetracycline in Mice and in Man: Possible Role in Microvesicular Steatosis Induced by This Antibiotic", Hepatology, vol. 8, No. 5, pp. 1056–1062, 1988.

Freneaux, et al., "Stereoselective and Nonstereoselective Effects of Ibuprofen Enantiomers on Mitochondrial beta–Oxidation of Fatty Acids", J. Pharm. Exp. Ther., vol. 255, No. 2, pp. 529–535, 1990.

Friis and Bundgaard, "Prodrugs of phosphates and phosphonates: Novel lipophilic alpha–acyloxyalkyl ester derivatives of phosphate–or phosphonate containing drugs masking the negative charges of these groups", Eur. J. Pharm. Sci., vol. 4, pp. 49–59, 1996.

Fromenty, et al., "Tianeptine a New Tricyclic Antidepressant Metabolized by beta–Oxidation of its Hepatanoic Side Chain, Inhibits the Mitochondrial Oxidation of Medium and Short Chain Fatty Acids in Mice", Biochem. Pharm., vol. 38, No. 21, pp. 3743–3751, 1989.

Fromenty, et al., "Dual Effect of Amiodarone on Mitochondrial Respiration. Initial Protonophoric Uncoupling Effect Followed by Inhibition of the Respiratory Chain at the Levels of Complex I and Complex II", J. Pharm. Exp. Ther., vol. 255, No. 3, pp. 1377–1384, 1990.

Hachisu et al, "Synthesis and Antihypertensive Activity of 5–O–Substituted Derivatives of 5–Hydroxypicolinic Acid", J. Pharm. Dyn., vol. 6, pp. 922–931, 1983.

Hague, et al., "Apoptosis in Colorectal Tumor Cells: Induction by the Short Chain Fatty Acids Butyrate, Propionate and Acetate and by the Bile Salt Deoxycholate", Int. J. Cancer, vol. 60, pp. 400–406, 1995.

Holmes, et al., "Preparation of Acylals and Analogs for Preparation of Biolabile Crosslinked Ultrasound Imaging Agents", Chem Abstracts, vol. 118, Abstract #191, 195e, 1993.

Ingram and Thomas, "The Electron Impact Induced Fragmentation of Geminal Dialkanoates", Organic Mass Spectrometry, vol. 12, No. 4, pp. 216–221, 1977.

Kamiya, et al., "Pharmaceutical Patches Comprising Water–Soluble Adhesive Sheet", Chem. Abstracts, vol. 126, Abstract #162263, 1997.

Kelloff, et al., "Chemoprevention Clinical Trials", Mutation Res., vol. 267, No. 2, pp. 291–295, 1992.

Kiso, et al., "Antihepatotoxic Principles of Curcuma longa Rhizomes", J. Medicinal Plant Res., vol. 49, pp. 185–187, 1983.

Klaveness, et al. "Polymers Containing Diester Units for Prosthetics and Dosage Forms", Chem Abstracts, vol. 117, Abstract #198,512u, 1992.

Le Dinh, et al., "Amineptine, a Tricyclic Antidepressant, Inhibits the Mitochondrial Oxidation of Fatty Acids and Produces Microvesicular Steatosis of the Liver in Mice", J. Pharm. Exp. Ther., vol. 247, No. 2, pp. 745–750, 1988.

Liu et al., "Cinnamic Acid: A Natural Product with Potential Use in Cancer Intervention", Int. J. Cancer, vol. 62 pp. 345–350, 1995.

Loftsson and Bodor, "Improved Delivery through Biological Membranes IX: Kinetics and Mechanism of Hydrolysis of Methylsulfinylmethyl 2–Acetoxybenzoate and Related Aspirin Prodrugs", J. Pharm. Sci., vol. 70, No. 7, pp. 750–755, 1981.

Los et al., "Synthesis of Some New Derivatives of 2–Hydroxy and 2–Acetyloxybenzoic Acids", Boll. Chim. Farm., vol. 121, pp. 285–302, 1982.

Man, et al., "Boron Fluoride Catalyzed Addition of Aliphatic Anhydrides to Aldehydes", J. Am. Chem. Soc., pp. 847–848, 1950.

Miller, et al., "Clinical Pharmacology of Sodium Butyrate in Patients with Acute Leukemia", Eur. J. Cancer Clin Oncol. vol. 23, No. 9, pp. 1283–1287, 1987.

Mosher and Kehr, "The Oxidation of Aliphatic Esters with Lead Tetraacetate", J. Am. Chem. Soc., vol. 82, pp. 5342–5345, 1960.

Nielsen and Bundgaard, "Evaluation of Glycolamide Esters and Various Other Esters of Aspirin as True Aspirin Prodrugs", J. Medicinal Chem., vol. 32, pp. 727–734, 1989.

Nordenberg., et al., "Biochemical and Ultrastructural Alterations Accompany the Anti–proliferative Effect of Butyrate on Melanoma Cells", Br. J. Cancer, vol. 55, pp. 493–497, 1987.

Novogrodsky et al., "Effect of Polar Organic Compounds on Leukemic Cells", Cancer, vol. 51, pp. 9–14, 1983.

Nudelman, et al., "Novel Anticancer Prodrugs of Butyric Acid", J. Med. Chem., vol. 35, pp. 687–694, 1992.

Oh, et al., "Convenient Synthesis of Geminal Biscarboxylates:Searching for an Efficient Route to HR 916B", Korean J. Med. Chem., vol. 6, No. 2, pp. 259–262, 1996.

Prasad, "Butyric Acid: A Small Fatty Acid with Diverse Biological Functions", Life Sci., vol. 27, No. 15, pp. 1351–1358, 1980.

Prasad, et al., "Decreased Expressions of c–myc and H–ras Oncogenes in Vitamin E Succinate Induced Morphologically Differentiated Murine B–16 Melanoma Cells in Culture", Biochem. Cell Bio., vol. 68, No. 11, pp. 1250–1255, 1990.

Rabizadeh, et al., "Rapid Alteration of c–myc and c–jun Expression in Leukemic Cells Induced to Differentiate By a Butyric Acid Prodrug", FEBS Lett, vol. 328, No. 3, pp. 225–229, 1993.

Ramain, et al., "Amineptine Hepatitis: Report of Two Cases", Gastroenterol. Clin. Biol., vol. 5, pp. 469–471, 1981.

Rephaeli, et al., "Butyrate–Induced Differentiation in Leukemic Myeloid Cells: in vitro and in vivo Studies", International Journal of Oncology, vol. 4, No. 6, pp. 1387–1391, 1994.

Riggs, et al., "n–Butyrate Causes Histone Modification in HeLa and Friend Erythroleukaemia Cells", Nature, vol. 268, No. 5617, pp. 462–464, 1977.

Roediger and Millard, "Selective Inhibition of Fatty Acid Oxidation in Colonocytes by Ibuprofen: A Cause of Colitis?", Gut, 36, pp. 55–59, 1995.

Rottleb, et al., "Structure–Activity Relationship of 17 Structural Analogues of N–Butyric Acid Upon c–myc Expression", Int. J. Cancer, vol. 67, pp. 724–729, 1996.

Safadi, et al, "Phosphoryloxymethyl Carbamates and Carbonates–Novel Water–Soluble Prodrugs for Amines and Hindered Alcohols", Pharm. Res., vol. 10, No. 9, pp. 1350–1355, 1993.

Sagawa, et al., "Agricultural Chemicals Based on Dialkyl Halomethyl Phosphates for Killing Insects, Worms and Bacteria", Chem. Abstracts, vol. 78, Abstract #132708g, 1973.

Samid, et al., "Phenylacetate: A Novel Nontoxic Inducer of Tumor Cell Differentiation", Cancer Research, 52, pp. 1988–1992, 1992.

Sanderson, et al., "Bleach Compositions", Chem. Abstracts, vol. 102, Abstract #47772t, 1985.

Scheeren and Tax, "Mixed Acylals; Synthesis of Alkylidene Carboxylate Formates", Synthesis, vol. 3, pp. 151–153, 1973.

Sher, et al., "Extended Therapy with Intravenous Arginine Butyrate in Patients with Beta—Hemoglobinopathies", New England Journal of Medicine, vol. 332, No. 24, pp. 1606–1610, 1995.

Smigel, "Nontoxic Drug Being Tested to Treat Cancer and Anemias", J. Nat'l Cancer Inst., vol. 84, No. 18, pp. 1398–1399, 1992.

Smith, et al., "Incorporation of Tributyrin Enhances the Expression of a Reporter Gene in Primary and Immortalized Cell Lines", Biotechniques, vol. 18, No. 5, pp. 852–855, 1995.

Srivastva and Farquhar, "Bioreversible Phosphate Protective Groups: Synthesis and Stability of Model Acyloxmethyl Phosphates", Biorganic Chemistry, vol. 12, pp. 118–129, 1984.

Srivastva, et al., "Mass Spectral Characterization of Acyloxymethyl Phosphates", J. Chem. Tech. Biotechnol., vol. 47, pp. 235–243, 1990.

Stamatoyannopoulos, et al., "Therapeutic Approaches to Hemoglobin Switching in Treatment of Hemoglobinopathies", Ann. Rev. Med., vol. 43, pp. 497–522, 1992.

Thiele, et al., "Cholesterol Lowering Agents", Chem. Abstracts, vol. #178,549n, 1975.

Thorne, et al., "Patterns of Histone Acetylation", Eur. J. Biochem., vol. 193, pp. 701–713, 1990.

Tomiska and Spousta, "Low–Molecular Polyoxymethylene Diacetates from Trioxane", Angew. Chem. Internat. Edit., vol. 1, No. 4, p. 211, 1962.

Toscani, et al., "Molecular Analysis of Sodium Butyrate–Induced Growth Arrest", Oncogene Res., vol. 3, No. 3, pp. 223–238, 1988.

Toyobo Co., "Electroconductive Resin Compositions", Chem. Abstracts, vol. 103, Abstract #125229h, 1985.

Vernia, et al., "Topical Treatment of Refractory Distal Ulcerative Colitis with 5–ASA and Sodium Butyrate", Digestive Diseases and Sciences, vol. 40, pp. 305–307, Feb. 1995.

Weinstein, "Cancer Prevention: Recent Progress and Future Opportunities", Cancer Res., vol. 51, pp. 5080s–5085s, 1991.

THERAPEUTIC AUGMENTATION OF OXYALKYLENE DIESTERS AND BUTYRIC ACID DERIVATIVES

FIELD OF THE INVENTION

This invention provides a method of augmenting the therapeutic activity of an oxyalkylene-containing compound, butyric acid, a butyric acid salt or butyric acid derivative by administering an inhibitor of β-oxidation of fatty acids to a patient or to host cells.

BACKGROUND OF THE INVENTION

The oxyalkylene-containing compound of this invention, butyric acid, butyric acid salts, and the butyric acid derivatives of this invention are used for treating, preventing or ameliorating cancer and other proliferative diseases as well as for inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, modulating gene expression and particularly augmenting expression of tumor suppressor genes, inducing tolerance to antigens, treating, preventing or ameliorating protozoan infection or inhibiting histone deacetylase in cells.

A method of potentiating the activities of the above compounds has been sought, particularly because some of these compounds exhibit short in vivo half-lives. One such method is to inhibit metabolism of these compounds by inhibiting the cellular β-oxidation cycle. Such inhibition would appear to prolong the half-life of the compounds in a patient or in cells and hence increase the duration of therapeutic effectiveness of the compounds. Alternatively, the dosages needed to obtain equivalent therapeutic effects can be lowered.

Several drugs have been shown to decrease mitochondrial β-oxidation of fatty acids, such as ibuprofen (Freneaux, et al., 1990, J. Pharmacol. Exp. Ther., 255:529–535), amineptine (Ramain, et al., 1981, Gastroenterol. Clin. Biol., 5:469–471; Le Dinh, et al., 1988, J. Pharmacol. Exp. Ther., 247:745–750), tianeptine (Fromenty, et al., 1989, Biochem. Pharmacol., 38:3743–3751), amiodarone (Fromenty, et al., 1990, Biochem. Pharmacol., 255:1377–1384), tetracycline (Zimmerman, et al., 1988, Hepatology, 8:1056–1062), and valproic acid and salicylic acid (Deschamps, et al., 1991, J. Pharmacol. Exp. Ther., 259:894–904). Many of the aforementioned drugs are non-steroidal antiinflammatory drugs (NSAIDs) These and those other compounds with substantially the same activity are termed β-oxidation inhibitors herein.

SUMMARY OF THE INVENTION

Accordingly, one embodiment of the present invention is directed to a method of augmenting the therapeutic activity of an oxyalkylene-containing compound, butyric acid, a butyric acid salt or butyric acid derivative which comprises administering to a patient or host cells an amount of an inhibitor of β-oxidation of fatty acids effective to inhibit the β-oxidation of the compound, acid, salt or derivative and thereby augment the therapeutic activity thereof, wherein said compound is represented by the formula:

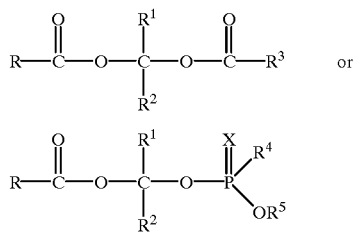

wherein
R is $C_3$ to $C_{10}$ alkyl, $C_3$ to $C_{10}$ alkenyl, $C_3$ to $C_{10}$ alkynyl, aryl, aralkyl, heteroaryl or heteroaralkyl, any of which can be optionally substituted with aryl, heteroaryl, halo, alkyl, alkoxy, hydroxy, amino, cyano, nitro, trifluoromethyl, carbonyl, acylamino, carbamoyl or a combination thereof;

$R^1$ and $R^2$ are independently H, $C_1$ to $C_{10}$ alkyl, $C_2$ to $C_{10}$ alkenyl, or $C_2$ to $C_{10}$ alkynyl, any of which can be optionally substituted with halo, alkoxy, amino, trifluoromethyl, aryl, heteroaryl or a combination thereof;

$R^3$ is
(1) $C_1$ to $C_{10}$ alkyl, $C_2$ to $C_{10}$ alkenyl, $C_2$ to $C_{10}$ alkynyl, aryl, aralkyl, heteroaryl or heteroaralkyl, any of which can be optionally substituted with aryl, heteroaryl, halo, alkyl, alkoxy, hydroxy, amino, cyano, nitro, trifluoromethyl, carbonyl, acylamino, carbamoyl or a combination thereof;

(2) —ACOOR$^6$, wherein A is aryl, heteroaryl, $C_1$ to $C_8$ alkyl, $C_2$ to $C_3$ alkenyl, or $C_2$ to $C_3$ alkynyl, wherein said alkyl, alkenyl or alkynyl is optionally substituted with one or more of hydroxy, halo, lower alkyl, alkoxy, carbonyl, thiol, lower alkylthio, aryl, heteroaryl or combination thereof, and further wherein $R^6$ is H, alkyl, alkenyl, aryl, aralkyl, heteroaryl, heteroaralkyl, or —CR$^1$R$^2$—O—C(O)—R;

(3)

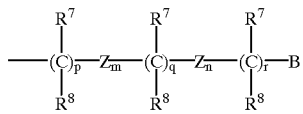

wherein Z is —CR$^9$=CR$^{10}$— or —C≡C—; $R^7$, $R^8$, $R^9$ and $R^{10}$ are independently H, alkyl or alkenyl; B is aryl or heteroaryl; m and n are independently integers from 0 to 5; the sum of m and n is from 1 to 5; and p, q and r are independently integers from 0 to 2;

(4) a nitrogen-containing heterocycloalkyl, heterocycloalkenyl, heteroaryl group or heteroaralkyl group, wherein the heteroaryl group and the heteroaralkyl group can have up to two additional substituents;

(5) an aryl or aralkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido, wherein the aryl or aralkyl groups can have up to two additional substituents;

(6) a $C_1$ to $C_{10}$ alkyl, $C_2$ to $C_{10}$ alkenyl, $C_3$ to $C_{10}$ alkynyl or $C_3$ to $C_7$ cycloalkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido;

(7) $C_1$ to $C_{12}$ alkyl or $C_2$ to $C_{10}$ alkenyl substituted with from one to ten substituents selected from the group consisting of hydroxy, alkoxy, acyloxy, aroyloxy and aryloxy, and, optionally having one or more halo groups, wherein adjacent hydroxy groups, if present, can optionally be present as an acetonide;

(8) —$(CH_2)_n$—[O—$(CH_2)_p]_m$—$OR^{11}$, —$(CH_2)_n$-PEG-$OH^{11}$, or —$(CH_2)_n$-PPG-$OR^{11}$; wherein $R^{11}$ is $C_1$ to $C_6$ alkyl, $C_2$ to $C_6$ alkenyl, aryl, acyl, aroyl, alkoxycarbonyl, aminocarbonyl or —$(CH_2)_n$—$COOCR^1R^2$—O—C(O)—R; PEG is a polyethylene glycol moiety having an average molecular weight of 200–8000; PPG is a polypropylene glycol moiety having an average molecular weight of 200–8000; p is an integer from 2 to 4; n is an integer from 1 to 5; and m is an integer from 1 to 6;

(9) together with the carbonyl group to which it is attached, an acyl moiety of an inhibitor of β-oxidation of fatty acids ($R^3CO$), wherein said first and second inhibitors are different;

X is oxygen or sulfur;

$R^4$ is independently H, $C_1$ to $C_6$ alkyl, $C_2$ to $C_6$ alkenyl, $C_2$ to $C_6$ alkynyl, aryl, aralkyl, heteroaryl, heteroaralkyl, —$OCR^1R^2$—O—C(O)—R or $OR^5$;

$R^5$ is independently H, $C_1$ to $C_6$ alkyl, $C_2$ to $C_6$ alkenyl, $C_2$ to $C_6$ alkynyl, aryl, aralkyl, heteroaryl, heteroaralkyl or —$CR^1R^2$—O—C(O)—R; and pharmaceutically-acceptable salts thereof.

In preferred embodiments, the compounds of the invention include (1) the alkyl oxyalkylene esters of pivaloyloxymethyl butyrate and butylidine dibutyrate.

(2) the tricarboxylic acid-containing oxyalkylene esters of mono-(butyroyloxymethyl)glutarate, bis-(butyroyloxymethyl)glutarate, mono-(1-butyroyloxyethyl)glutarate and bis-(1-butyroyloxyethyl)glutarate.

(3) the unsaturated oxyalkylene esters of cinnamoyloxymethyl butyrate, cinnamoyloxymethyl phenylacetate, cinnamoyloxymethyl 4-phenylbutyrate, 1-(cinnamoyl)oxyethyl phenylacetate, 1-(cinnamoyl)oxyethyl 4-phenylbutyrate, 3,4-dimethoxycinnamoyloxymethyl butyrate and 1-(3,4-dimethoxycinnamoyl)oxyethyl butyrate.

(4) the nitrogen-containing oxyalkylene esters of 4-(butyramido)butyroyloxymethyl butyrate, 4-(butyramido)benzoyloxymethyl butyrate, 4-aminobenzoyloxymethyl butyrate, 4-aminobenzoyloxymethyl butyrate hydrochloride, 1-(4-aminobenzoyloxy)ethyl butyrate, 3-pyridinecarboxymethyl butyrate, 1-(3-pyridinecarboxy)ethyl butyrate and (N-methylpyridinium)-3-carboxymethyl butyrate chloride.

(5) the hydroxy or ether-containing oxyalkylene esters of 2-(2-methoxyethoxy)acetyloxymethyl butyrate, 2-[2-(methoxyethoxy)ethoxy]acetyloxymethyl butyrate, 1-[2-(2-methoxyethoxy)acetyl]oxyethyl butyrate and 1-{2-[2-(2-methoxyethoxy)ethoxy]acetyl}oxyethyl butyrate.

(6) the metabolically-stabilized oxyalkylene esters of α-methyl-4-(2-methylpropyl)-benzeneacetyloxymethyl butyrate, 1-{α-methyl-4(2-methylpropyl)-benzeneacetyloxy}-ethyl butyrate, 1-{α-methyl-4(2-methylpropyl)-benzeneacetyloxy}-butyl butyrate, 6-methoxy-α-methyl-2-naphthaleneacetyloxylmethyl butyrate, 1-{6-methoxy-α-methyl-2-naphthaleneacetyloxy}-ethyl butyrate and 1-{6-methoxy-α-methyl-2-naphthaleneacetyloxy}-butyl butyrate.

(7) the oxyalkylene phosphate compounds of butyroyloxymethyl diethyl phosphate, 1-(1-butyroyloxy)ethyl diethyl phosphate, mono(butyroyloxymethyl) phosphate and 1-{1-(4-phenylbutyroyloxy)ethyl} diethyl phosphate.

(8) the sodium, arginine and lysine salts of butyric acid, and more preferably arginine butyrate, (9) the butyric acid derivatives isobutyramide, monobutyrin, tributyrin, 2-phenylbutyric acid, 3-phenylbutyric acid, 4-phenylbutyric acid, phenylacetic acid, cinnamic acid, α-methyldihydrocinnamic acid and chloropropionic acid.

The inhibitors of β-oxidation can be ketoprofen, diflunisal, salsalate, etodolac, tolmetin, ibuprofen, naproxen, oxaprozin, salicylic acid, acetylsalicylic acid, indomethacin, flurbiprofen, diclofenac, mefenamic acid, meclofenamic acid, ketorolac, sulindac, valproic acid or 2-valproenic acid.

Another aspect of the invention is directed to a pharmaceutical composition for augmenting the therapeutic activity of an oxyalkylene-containing compound, butyric acid, a butyric acid salt or a butyric acid derivative which comprises a therapeutically-effective amount of said compound, acid, salt or derivative and an amount of a first inhibitor of β-oxidation of fatty acids effective to inhibit the β-oxidation of said compound, acid, salt or derivative, and thereby augment the therapeutic activity thereof, in admixture with a pharmaceutically acceptable carrier. The pharmaceutical compositions contain the same oxyalkylene-containing compounds, butyric acid salts and butyric acid derivatives as used in the methods of the invention. The preferred compositions contain the same preferred compounds as used in the subject methods.

In addition, the present invention is also directed to the above pharmaceutical compositions further containing a pharmaceutical agent selected from a cytokine, an interleukin, an anti-cancer agent, a chemotherapeutic agent, an antibody, a conjugated antibody, an immune stimulant, an antibiotic, a hormone antagonist, a growth stimulant, an antiviral agent or a cytotoxic agent.

DETAILED DESCRIPTION OF THE INVENTION

The present invention is directed to a method of augmenting therapeutic activity of certain compounds susceptible to β-oxidation by inhibiting or decreasing the β-oxidation thereof by administering therapeutic dosages of those compounds to a patient or host cells together with an amount of a β-oxidation inhibitor effective to provide augment the therapeutic activity. In general augmentation of therapeutic activity means that the duration of the therapeutic effect of a particular compound (i.e., the oxyalkylene-containing compounds, butyric acid, butyric acid salts or butyric acid derivatives of the invention, also collectively referred to herein as the compounds of the invention) will last for a longer period, i.e., exhibit a longer duration of therapeutic effectiveness, in a patient or host cells than it normally would in the absence of the β-oxidation inhibitor. Augmentation of therapeutic activity includes enhancement of that activity. Furthermore, administering a β-oxidation inhibitor with a particular compound of the invention can also cause synergistic effects and allow administration of lower doses of that compound than would be needed to achieve the same therapeutic effectiveness in the absence of the β-oxidation inhibitor.

In accordance with the invention, the therapeutic activities which can be subject to augmentation are used for treating, preventing or ameliorating cancer and other proliferative diseases as well as for inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, modulating gene expression and particularly augmenting expression of tumor suppressor genes, inducing tolerance to antigens or treating, preventing or ameliorating protozoan infection or inhibiting histone deacetylase in cells as explained below in greater detail.

In one embodiment, the therapeutic activity is effective to treat, prevent or ameliorate cancer and other proliferative disorders. The compounds of the invention are particularly useful for treating, preventing or ameliorating the effects of cancer and other proliferative disorders by acting as anti-proliferative or differentiating agents in subjects afflicted with such anomalies. Such disorders include but are not limited to leukemias, such as acute promyelocytic leukemia, acute myeloid leukemia, and acute myelomonocytic leukemia, other myelodysplastic syndromes, multiple myeloma such as but not limited to breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. It is also possible that compounds of the invention have anti-proliferative effects on non-cancerous cells as well, and may be of use to treat benign tumors and other proliferative disorders such as psoriasis. In a preferred embodiment the therapeutic activity is effective to treat or ameliorate leukemia, squamous cell carcinoma and neuroblastoma.

Still further the therapeutic activity is effective to treat, prevent or ameliorate cancer and other proliferative disorders by inhibiting histone deacetylase in a patient or by inducing cellular apoptosis of cancer cells or proliferating cells in a proliferative disorder.

In another embodiment, the therapeutic activity is effective to cause differentiation of or block proliferation of cancerous or neoplastic cells.

In still another embodiment method, the therapeutic activity is effective to inhibit telomerase activity in cancer cells. For example, decreasing the telomerase activity of the cells can inhibit the malignant progression of the cells. This method can be applied to in vivo or in vitro cells.

In yet another embodiment of this invention, the method includes further administering a therapeutically-effective amount of an antiviral agent, thus rendering the therapeutic activity effective to treat, prevent or ameliorate virus-associated tumors. The antiviral agent can be administered pre-, post or simultaneously with the other compounds of the method. Antiviral agents contemplated for use in the invention include ganciclovir, acyclovir and famciclovir, and preferably ganciclovir. The virus-associated tumors which can be treated, prevented or ameliorated in accordance with the invention include, but are not limited to, EBV-associated malignancy, Kaposi's sarcoma, AIDS-related lymphoma, hepatitis B-associated malignancy or hepatitis C associated malignancy. EBV-associated malignancies include nasopharyngeal carcinoma and non-Hodgkins'0 lymphoma and are preferred embodiments of the invention.

Yet a further embodiment is directed to the method of the invention which additionally includes administering a therapeutically-effective amount of a pharmaceutical agent to thereby enhance the activity of these agents. This embodiment is useful in treating, preventing or ameliorating cancer and other proliferative disorders in a patient suffering from such disorders. The pharmaceutical agents of the invention for the above method include, but are not limited to, cytokines, interleukins, anti-cancer agents, chemotherapeutic agents, antibodies, conjugated antibodies, immune stimulants, antibiotics, hormone antagonists, and growth stimulants. The β-oxidation inhibitor and compounds of the invention can be administered prior to, after or concurrently with any of the agents.

Still another embodiment of the invention is provided by further administering a therapeutically-effective amount of cytotoxic agent with the compound of the invention and the first β-oxidation inhibitor. In this instance, the therapeutic activity is effective to ameliorate the effects of the cytotoxic agent in a mammalian patient by inducing growth arrest of rapidly-proliferating epithelial cells of the patient and thereby protect those cells from the cytotoxic effects of the agent. The cytotoxic agent can be a chemotherapeutic agent, an anticancer agent, or radiation therapy. Rapidly proliferating epithelial cells are found in hair follicles, the gastrointestinal tract and the bladder, for example. Such cells include hair follicle cells, or intestinal cryt cells. Rapidly proliferating cells are also found in the bone marrow and include bone marrow stem cells. In accordance with the invention the cytotoxic agent and the other compounds of the invention can be administered simultaneously, or the cytotoxic agent can be administered prior to or after the other compounds. Administration (simultaneously or separately) can be done systemically or topically as determined by the indication. In addition, when the cytotoxic agent is radiation therapy, the other compounds of the invention can be administered to a cancer patient pre- or post-radiation therapy to treat or ameliorate the effects of cancer.

In a further embodiment, the therapeutic activity is effective to modulate an immune response in a patient. Modulation of the immune response includes enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation, or a combination thereof.

In a still further embodiment, the therapeutic activity is effective to treat a blood disorder in a patient. The blood disorders treatable in accordance with the invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. In this regard, the therapeutic activity can be effective to increase the hemoglobin content in blood of a patient.

Still further the therapeutic activity is effective to induce wound healing, treat cutaneous ulcers or treat a gastrointestinal disorder. Cutaneous ulcers include leg and decubitus ulcers, stasis ulcers, diabetic ulcers and atherosclerotic ulcers. With respect to wound healing, method is useful for treating abrasions, incisions, burns, and other wounds. Gastrointestinal disorders include colitis, inflammatory bowel disease, Crohn's disease and ulcerative colitis.

Further still the therapeutic activity is effective to modulate gene expression in a host or host cells by enhancing, augmenting or repressing the expression of a gene of interest, preferably a butyric acid-responsive gene. When expression of the gene of interest is to be enhanced or augmented, the gene can encode a gene product which is or acts as a repressor of another gene, a tumor suppressor, an inducer of apoptosis or an inducer of differentiation. When expression of the gene of interest is to be repressed, the gene can encode a gene product which is or acts as an oncogene or an inhibitor of apoptosis. For example, the bcl-2 gene encodes an inhibitor of apoptosis.

More particularly, the therapeutic activity is effective to augment gene expression, especially of a tumor suppressor gene, a butyric acid-responsive gene or a fetal hemoglobin gene, in a host or host cells. Preferably the host is a cancer patient. This method of the invention includes augmenting tumor suppressor gene expression in conjunction with ex vivo or in vivo gene therapy, i.e., the compounds of the invention can be co-administered to the host during administration of gene therapy vectors or administration of the ex vivo transfected cells. Similarly, the method of the invention can be used for treating cells during the transfection step of ex vivo gene therapy. The hosts of the method therefore include cancer patients or other patients under going gene therapy. The host cells of the invention include hematopoietic cells such as stem cells and progenitor cells, e.g., or any other cell type used in ex vivo gene therapy.

In yet a further embodiment, the therapeutic activity is effective to enhance insulin expression in an insulin-dependent patient.

In yet another embodiment, the therapeutic activity is effective to enhance chloride channel expression in a cystic fibrosis patient.

In a further embodiment, the therapeutic activity is effective to enhance recombinant gene expression in a recombinant host cell containing an expression system for a butyric acid-responsive gene. The host cells can be mammalian cells, insect cells, yeast cells or bacterial cells and the correspondingly known expression systems for each of these host cells. The gene can encode any protein or peptide of interest, expression of which can be regulated or altered by butyric acid or a butyric acid salt. A butyric acid-responsive gene is a gene that has a promoter, enhancer element or other regulon that modulates expression of the gene under its control in response to butyric acid or a salt of butyric acid. For example, genes contemplated for regulation in accordance with the invention include but are not limited to tumor suppressor genes (such as p53) and the γ-globin chain of fetal hemoglobin.

In yet another embodiment, the therapeutic activity is effective to induce tolerance to an antigen. Preferably the antigen is a self-antigen. For example, the self antigen can be associated with an autoimmune disease, such as systemic lupus erythromatosus, rheumatoid arthritis, multiple sclerosis or diabetes. Alternatively, the antigen can be present on a transplanted organ or cells.

In yet a further embodiment, the therapeutic activity is anti-protozoan activity. Hence this method can be used to to treat, prevent or ameliorating protozoan infection in a patient. The anti-protozoan activities, include but are not limited to, anti-malarial anti-cryptosporidiosis, anti-toxoplasmosis, or anti-coccidiosis activity. Anti-protozoan activity can be exerted by inhibiting protozoan histone deacetylase in a patient.

In a still further embodiment, the therapeutic activity is effective to inhibit histone deacetylase in host cells.

The oxyalkylene-containing compounds and other compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein, "alkyl" means both branched- and straight-chain, saturated aliphatic hydrocarbon groups having the specified number of carbon atoms. As used herein "lower alkyl" means an alkyl group having 1 to 5 carbon atoms. As used herein, "alkenyl" means hydrocarbon chains of either a straight or branched configuration and one or more unsaturated carbon-carbon bonds, such as ethenyl, propenyl, and the like. "Lower alkenyl" is an alkenyl group having 2 to 6 carbon atoms. As used herein, "alkynyl" means hydrocarbon chains of either a straight or branched configuration and one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl or use of any of these terms with another moiety, e.g., aralkyl, means lower alkyl, lower alkenyl and lower alkynyl, respectively.

When alkyl, alkenyl, and alkynyl, or a variation thereof such as lower alkyl, are used to define the A moiety of $R^3$ (or any other group that has two appendages) then these groups have the meanings as defined herein except that each term refers to a hydrocarbon chain having the specified number of carbon atoms. Similarly, when aryl and heteroaryl are used to define the A moiety, then these groups have the meanings defined herein except that there are two attachment points on the aromatic ring. When A is an alkyl chain, one preferred A moiety has up to three lower alkyl substituents and, even more preferably, up to three methyl groups.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. The presence of substitution on the aryl group is optional, but when present, the substituents can be halo, alkyl, alkoxy, hydroxy, amino, cyano, nitro, trifluoromethyl, acylamino, carboxy, carboxyalkyl or carbamoyl.

As used herein, the term "heteroaryl" includes "heteroaryl" and "substituted heteroaryl." Thus "heteroaryl" of this invention means a stable 5- to 10-membered monocyclic or bicyclic heterocyclic ring which is aromatic, and which consists of carbon atoms and from 1 to 3 heteroatoms selected from the group consisting of N, O and S and wherein the nitrogen may optionally be quaternized, and including any bicyclic group in which any of the above-defined heteroaryl rings is fused to a benzene ring. The heteroaryl ring may be attached to its pendant group at any heteroatom or carbon atom which results in a stable structure. The presence of substitution on the heteroaryl group is optional and can be on a carbon atom, a nitrogen atom or other heteroatom if the resulting compound is stable and all the valencies of the atoms have been satisfied. When present, the substituents of the substituted heteroaryl groups are the same as for the substituted aryl groups and also include alkylammonium salts when the substituent is an alkyl group attached to the nitrogen atom of the heteroaryl ring. These quaternized ammonium salts include halides, hydrohalides, sulfates, methosulfates, methanesulfonates, toluenesulfonates, nitrates, phosphates, maleates, acetates, lactates or any other pharmaceutically acceptable salt. Examples of heteroaryl groups include, but are not limited to, pyridyl, pyrimidinyl, furanyl, thienyl, pyrrolyl, pyrazolyl, imidazolyl, tetrazolyl, benzofuranyl, benzothienyl, indolyl, indolenyl, quinolinyl, isoquinolinyl and benzimidazolyl.

As used herein, "aralkyl" and "heteroaralkyl" refer to an aryl or heteroaryl group attached to an alkyl group. The aryl and heteroaryl groups of this moiety can optionally be substituted in accordance with the definitions herein. Examples of heteroaralkyl groups include but are not limited to 2-, 3-, or 4-pyridylmethyl and 3-(2-, 3- or 4-pyridyl) propyl and the like.

The term "substituted", as used herein, means that one or more hydrogens on the designated atom are replaced with a selection from the indicated groups, provided that the designated atom's normal valency is not exceeded, and that the substitution results in a stable compound.

The substituents of the invention include, as indicated, halo, hydroxy, alkyl, alkoxy, amino, cyano, nitro, trifluoromethyl, aryl, heteroaryl, monoalkylamino, dialkylamino, trialkylammonium and salts thereof, carbamoyl, carboxy, carbonyl, carboxamide, carbalkoxy, acylamino, arylcarbonylamino, alkoxycarbonylamino, formamido, guanidino, ureido, sulfamyl, and alkylsulfonamido. These groups can be substituents for alkyl, alkenyl, alkynyl, cycloalkyl, aryl, aralkyl, heteroaryl and heteroaralkyl groups as indicated in accordance with the invention. A "halo" group is a halogen, and includes fluoro, chloro, bromo and iodo groups. The term "alkoxy" refers to an alkyl group having at least one oxygen substituent represented by R—O—. The group "acylamino" is represented by the formula R—C(O)—NH— where R is alkyl. "Arylcarbonylamino" and "alkoxycarbonylamino" are similar to acylamino except that the R is aryl or alkoxy, respectively.

As used herein, "PEG" is a polyethylene glycol moiety having the formula —(OCH$_2$CH$_2$)$_x$, where x is that number of subunits required to give an average molecular weight ranging from about 200 to about 8000. As used herein, "PPG" is a polypropylene glycol moiety having the formula —(OCH$_2$CH$_2$CH$_2$)$_x$, where x is that number of subunits required to give an average molecular weight ranging from about 200 to about 8000.

When R$^3$ is R$^3$CO, the oxyalkylene ester compounds have covalently attached thereto an acyl moiety that inhibits beta-oxidation of fatty acids. The β-oxidation inhibitor that forms part of the acyl moiety can be the same as or different from the free β-oxidation inhibitor administered in accordance with the methods of the invention. The acyl component can thus be, for example, that of a cyclooxygenase 1 or 2 inhibitor which acts on the arachidonic acid cascade, such as a salicylic acid derivative such as salsalate, diflunisal, sulfasalazine, an indole or indene acetic acid, such as indomethacin, sulindac, etodolac, and the like; a heteroaryl acetic acid such as tolmetin, diclofenac, or ketorolac; an anthranilic acid such as mefenamic acid or meclofenamic acid; or a propionic acid derivative such as naproxen, flurbiprofen, ketoprofen, fenoprofen, oxaprozin; or valproic acid or 2-valproenic acid and the like. These particular acyl-containing oxyalkylene ester compounds of the present invention have enhanced activity, i.e., enhanced stability, and exhibit longer duration of action than other known oxyalkylene ester compounds, butyric acid, sodium butyrate and arginine butyrate. It is believed that the covalent attachment of a beta-oxidation inhibitor in the present compounds is responsible, at least in part, for the enhanced stability and potency of this class of compounds.

As used herein, "butyric acid derivative" is isobutyramide, monobutyrin, tributyrin, 2-phenylbutyric acid, 3-phenylbutyric acid, 4-phenylbutyric acid, phenylacetic acid, cinnamic acid, α-methyldihydrocinnamic acid, 3-chloropropionic acid or vinyl acetic acid.

As used herein, "therapeutically-effective amount" refers to that amount necessary to administer to a host to achieve the indicated therapeutic effect, and includes but is not limited to, the amount to achieve an anti-tumor effect; to induce differentiation and/or inhibition of proliferation of malignant cancer cells, benign tumor cells or other proliferative cells; to aid in the chemoprevention of cancer; to promote wound healing; to treat a gastrointestinal disorder; to treat a blood disorder or increase the hemoglobin content of blood; to modulate an immune response; to enhance recombinant gene expression; to modulate gene expression; to augment expression of tumor suppressor genes; to enhance insulin expression; to enhance chloride channel expression; to induce tolerance to an antigen; to treat, prevent or ameliorate protozoan infection; or to inhibit histone deacetylase in cells. Methods of determining therapeutically-effective amounts are well known.

When the therapeutic or effective amount of the compound is for treating, preventing or ameliorating cancer or other proliferative disorder, then that amount can be an amount effective to inhibit histone deacetylase in the subject, patient or cancerous cells. Similarly, when the therapeutic or effective amount of the compound is for treating, preventing, or ameliorating protozoan infection then that amount can be an amount effective to inhibit protozoan histone deacetylase in the subject, patient or cancerous cells.

As used herein, "pharmaceutically acceptable salts" refer to salts of the disclosed compounds that are modified by making acid or base salts. Examples include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfates, toluenesulfonates, nitrates, phosphates, maleates, acetates, lactates and the like. Pharmaceutically-acceptable salts of the compounds of the invention can be prepared by reacting the free acid or base forms of these compounds with a stoichiometric or greater amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences,* 17th ed., Mack Publishing Company, Easton, Pa., 1985, p. 1418, the disclosure of which is hereby incorporated by reference in its entirety. Pharmaceutically acceptable salts also include amino acid salts such as arginine and lysine salts.

The "pharmaceutical agents" for use in the methods of the invention include, but are not limited to, anticancer agents as well as differentiating agents. Further, the pharmaceutical agent can be a cytokine, an interleukin, an anti-cancer agent, a chemotherapeutic agent, an antibody, a conjugated antibody, an immune stimulant, an antibiotic, a hormone antagonist or a growth stimulant. The pharmaceutical agent can also be a cytotoxic agent or an antiviral agent. Cytotoxic agents include antiviral nucleoside antibiotics such as ganciclovir, acyclovir, and famciclovir. These latter compounds are act as antiviral agents. Cytotoxic agents can also include radiation therapy.

As used herein, the "chemotherapeutic agents" include but are not limited to alkylating agents, purine and pyrimidine analogs, vinca and vinca-like alkaloids, etoposide and etoposide-like drugs, corticosteroids, nitrosoureas, antimetabolites, platinum-based cytotoxic drugs, hormonal antagonists, anti-androgens and antiestrogens.

The "cytokines" for use herein include but are not limited to interferon, preferably α, β or γ interferon, as well as IL-2, IL-3, G-CSF, GM-CSF and EPO.

As used herein, an "immune stimulant" is a substance such as $C.\ parvum$ or sarcolectin which stimulates a humoral or cellular component of the immune system.

The "chemotherapeutic agents" of the invention include but are not limited to tamoxifen, doxorubicin, L-asparaginase, dacarbazine, amsacrine, procarbazine, hexamethylmelamine, mitoxantrone and gemcitabine.

SYNTHETIC METHODS

The compounds of the present invention can generally be prepared by any method known in the art, are readily available or can be obtained commercially. For example, certain oxyalkylene compounds of the invention can be made by reacting the acid RCOOH with a reagent of the formula

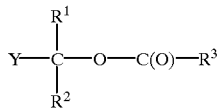

or by similar reactions between any of the appropriate acids and the appropriate alkyl halides in the presence of a base, where Y is a leaving group such as halogen, methanesulfonate or p-toluenesulfonate and R, $R^1$, $R^2$ and $R^3$ are as defined herein.

Alternatively, some of the compounds of the present invention may be made by reacting the acid RCOOH with a reagent of the formula

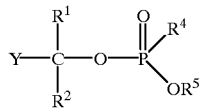

wherein Y is a leaving group such a halogen, methanesulfonate or p-toluenesulfonate and X, R, $R^1$, $R^2$, $R^4$ and $R^5$ are as defined herein above, in the presence of a base or with a salt of the acid, such as a silver or trialkylammonium salt.

In carrying out the synthesis reactions above, it may be desirable to protect certain functional groups, such as amines or hydroxyl groups by the use of standard protecting groups.

Phosphorothioate derivatives can be prepared according to procedures known in the art, e.g., by reaction of the appropriate compounds, with phosphorus pentasulfide or other sulfurating agent, in the presence of an inert solvent.

The above reagents are readily prepared according to literature procedures, see for example, Nudelman et al., $J.\ Med.\ Chem.$ 35:687–694, 1992, and Japanese patent 07033709 (1995). The base can be a trialkylamine, pyridine, an alkali metal carbonate or other suitable base. The reaction can be carried out in the presence or absence of an inert solvent. Suitable solvents include, for example, acetone, benzene, toluene, tetrahydrofuran, ethyl acetate, acetonitrile, dimethylformamide, dimethyl sulfoxide, chloroform, dioxan or 1,2-dichloroethane.

Specific protocols for making many of the compounds listed in (1) to (7) above in the "Summary of the Invention" are also provided in (1) U.S. Pat. No. 5,200,553, (2) co-pending application entitled "TRICARBOXYLIC ACID-CONTAINING OXYALKYL ESTERS AND USES THEREOF," (3) co-pending application entitled "UNSATURATED OXYALKYLENE ESTERS AND USES THEREOF," (4) co-pending application entitled "NITROGEN-CONTAINING OXYALKYLENE ESTERS AND USES THEREOF," (5) co-pending application entitled "HYDROXY AND ETHER-CONTAINING OXYALKYLENE ESTERS AND USES THEREOF," (6) co-pending application entitled "METABOLICALLY STABILIZED OXYALKYLENE ESTERS AND USES THEREOF," and (7) co-pending application entitled "OXYALKYLENE PHOSPHATE COMPOUNDS AND USES THEREOF," respectively, which are incorporated herein by reference.

The procedures outlined above can be improved by one skilled in the art by, for instance, changing the temperature, duration, stoichiometry or other parameters of the reactions. Any such changes are intended to fall within the scope of this invention.

ACTIVITY

The therapeutic activities of the invention can be measured or assessed using generally-accepted techniques known to those skilled in the art consistent with the activity of interest. For example, the activity of compounds useful as differentiating agents can be measured using standard methodology of the nitro-blue tetrazolium reduction assay (e.g., Rabizadeh et al., $FEBS\ Lett.$ 328:225–229, 1993; Chomienne et al., $Leuk.\ Res.$ 10:631, 1986; and Breitman et al. in $Methods\ for\ Serum\mbox{-}free\ Culture\ of\ Neuronal\ and\ Lymphoid\ Cells$, Alan R. Liss, N.Y., p. 215–236, 1984 which are hereby incorporated by reference in their entirety) and as described below. This in vitro assay has been deemed to be predictive and in fact correlative with in vivo efficacy (Castaigne et al., $Blood$ 76:1704–1709, 1990).

Another assay which is predictive of differentiating activity is the morphological examination for the presence of Auer rods and/or specific differentiation cell surface antigens in cells collected from treatment groups, as described in Chomienne et al., ($Blood$ 76:1710–1717, 1990 which is hereby incorporated by reference in its entirety) and as described below.

The anti-proliferation activity of compounds of the present invention can be determined by methods generally known to those skilled in the art. Generally-accepted assays for measuring viability and anti-proliferative activity are the trypan blue exclusion test and incorporation of tritiated thymidine, also as described by Chomienne, et al., above, which is incorporated herein by reference. Other assays which predict and correlate antitumor activity and in vivo efficacy are the human tumor colony forming assay described in Shoemaker et al., *Can. Res.* 45:2145–2153, 1985, and inhibition of telomerase activity as described by Hiyayama et al., *J. Natl. Cancer Inst.* 87:895–908, 1995, which are both incorporated herein by reference in their entirety. These assays are described in further detail below.

Cell Cultures

Human promyelocytic leukemia cells (HL-60), human pancreatic carcinoma cells (PaCa-2) and human breast adenocarcinoma cells, pleural effusion cells (MCF-7) can be cultured as follows. Cells are grown in RPMI media with 10% FCS, supplemented with 2 mM glutamine and incubated at 37° C. in a humidified 5% $CO_2$ incubator. Alternatively, cells can be grown in any other appropriate growth medium and conditions which supports the growth of the cell line under investigation. Viability can be determined by trypan blue exclusion. Cells are exposed to a test compound, cultures are harvested at various time points following treatment and stained with trypan blue.

Mass Balance Determination

The metabolism of a test compound, e.g., an oxyalkylene-containing compound or a butyric acid salt or derivative, can be followed by administering radiolabelled compound by intravenous, intraperitoneal or per os route to a mouse and identifying the nature and quantity of radiolabelled-compounds released or present in the blood, excreta and tissues as well as during respiration.

For example, C57BL/6 mice can be injected injected with 20–500 mg/kg of a test compound (5 $\mu$Ci) and 0.01–5 mg/kg NSAID compound i.v., i.p. or p.o., and placed in metabolic cages so that expired $CO_2$ and volatile organics can be trapped chemically. Blood, urine, and feces are collected at various times. Total radioactivity in the blood, urine, expired $CO_2$, and volatile traps is determined by solubilizing the sample and scintillation counting. Feces and carcasses are homogenized and subjected to scintillation counting to determine total radioactivity.

Blood samples can be extracted with acetonitrile and run on an HPLC system to separate radiolabelled test compound, butyric acid and other metabolites. The amount of radioactivity can be determined with an on-line scintillation flow detector. HPLC fractions can also be collected and monitored. The clearance of the test compound from the blood is measured and its half-life is estimated.

Cellular Staining to Detect Differentiation

Lipid staining and/or immunochemical staining of casein can be used as a marker for cellular differentiation of breast cancer cells (Bacus et al., *Md. Carcin.* 3:350–362, 1990). Casein detection can be done by histochemical staining of breast cancer cells using a human antibody to human casein as described by Cheung et al., *J. Clin. Invest.* 75:1722–1728, which is incorporated by reference in its entirety.

Nitro-Blue Tetrazolium (NBT) Assay

Cell differentiation of myeloid leukemia cells can be evaluated, for example, by NBT reduction activity as follows. Cell cultures are grown in the presence of a test compound for the desired time period. The culture medium is then brought to 0.1% NBT and the cells are stimulated with 400 mM of 12-O-tetradecanoyl-phorbol-13-acetate (TPA). After incubation for 30 min at 37° C., the cells are examined microscopically by scoring at least 200 cells. The capacity for cells to reduce NBT is assessed as the percentage of cells containing intracellular reduced black formazan deposits and corrected for viability.

Cell Surface Antigen Immunophenotyping

Cell surface antigen immunotyping can be conducted using dual-color fluorescence of cells gated according to size. The expression of a panel of antigens from early myeloid (CD33) to late myeloid can be determined as described in Warrell, Jr. et al., *New Engl. J. Med.* 324:1385–1392, 1992, which is incorporated by reference herein in its entirety.

Apoptosis Evaluation

Apoptosis can be evaluated by DNA fragmentation, visible changes in nuclear structure or immunocytochemical analysis of Bcl-2 expression.

DNA fragmentation can be monitored by the appearance of a DNA ladder on an agarose gel. For example, cellular DNA is isolated and analyzed by the method of Martin et al., *J. Immunol.*, 145:1859–1867, 1990 which is incorporated by reference herein in its entirety.

Changes in nuclear structure can be assessed, for example, by acridine orange staining method of Hare et al., *J. Hist. Cyt.*, 34:215–220, 1986 which is incorporated by reference herein in its entirety.

Immunological detection of Bcl-2 can be performed on untreated cells and cells treated with the test compound. HL-60 cells are preferred but other cell lines capable of expressing Bcl-2 can be used. Cytospins are prepared and the cells are fixed with ethanol. Fixed cells are reacted overnight at 4° C. with the primary monoclonal antibody, anti-Bcl-2 at a dilution of 1:50. Staining is completed to visualize antibody binding, for example, using Strep A-B Universal Kit (Sigma) in accordance with the manufacturer's instructions. Identically-treated cells which received no primary antibody can serve as a non-specific binding control. Commercial kits are also available and can be used for detecting apoptosis, for example, Oncor's Apop Tag®.

Modulation of Gene Expression

The levels of expression from oncogene and tumor suppressor genes can be evaluated by routine methods known in the art such as Northern blotting of RNA, immunoblotting of protein and PCR amplification.

Mouse Cancer Model

Compounds can be examined for their ability to increase the life span of animals bearing B16 melanomas, Lewis lung carcinomas and myelomonocytic leukemias or to reduce lung metastatic lesions as described in Nudelman et al., *J. Med. Chem.* 35:687–694, 1992, or Rephaeli et al., *Int. J. Cancer* 49:66–72, 1991, which are incorporated by reference herein in their entireties.

For example, the efficacy of compounds of the present invention in a leukemia model can be tested as follows: Balb/c mice are injected with WEHI cells and a test compound or control solution is administered the following day. The life span of the treated animals is compared to that of untreated animals.

The efficacy of compounds of the present invention on primary tumors can also be tested with subcutaneously implanted lung carcinoma or B16 melanoma by measuring the mass of the tumor at the site of implantation every two weeks in control and treated animals.

The efficacy of compounds in xenografts can be determined by implanting the human tumor cells subcutaneously into athymic mice. Human tumor cell lines which can be used include, but are not limited to, prostate carcinoma (human Pc-3 cells), pancreatic carcinoma (human Mia PaCa cells), colon adenocarcinoma (human HCT-15 cells), neuroblastoma, pleural effusion and mammary adenocarcinoma (human MX-1 cells). Treatment with control solution or a test compound of the invention begins, for example, when tumors are approximately 40–100 mg. Anti-tumor activity is assessed by measuring the delay in tumor growth, and/or tumor shrinking and/or increased survival of the treated animals relative to control animals. Xenograft models can also be assessed as described in Dahiya et al., *Biochem. Mol. Biol. Intl.* 35:487–498, 1995 and Jankyn et al., *Cancer Res.* 57:559–563, 1997.

Telomerase Activity

High levels of telomerase activity is associated with the high proliferation rate found in cancer cells. Compounds which inhibit telomerase activity results in inhibition of cancer cell growth and de-differentiation. Commercially available telomerase assays can thus be used to assess the anticancer activities of compounds on cancer cell lines.

Chemoprevention

The chemoprevention activity of the compounds of the invention can be determined in the two-stage mouse carcinogenesis model of Tatsuta, et al., *Carcinogenesis* 17: 293–296, 1996, or Smith et al., *Carcinogenesis* 17: 809–813, 1996. In this regard, any compound containing a butyric acid moiety and a para-aminobenzoic acid moiety (PABA) is expected to have good chemoprevention activity since it can release two active compounds when hydrolyzed by cellular or blood esterases. PABA is associated with antimutagenic activity. (Semenov et al., 1994, *Vopr. Med. Khim.* 40:48).

Assay of Compounds

Compounds of the invention, their salts or metabolites, can be measured in a biological sample by any method known to those skilled in the art of pharmacology, clinical chemistry or the like. Such methods for measuring these compounds are standard methods and include, but are not limited to high performance liquid chromatography (HPLC), gas chromatography (GC), gas chromatography mass spectroscopy (GC-MS), radioimmunoassay (RIA), and others.

Dosage and Formulation

The compounds of the present invention can be administered to a mammalian patient by any means that produces contact of the active agent with the agent's site of action in the body of the subject. Mammalian patients include humans and domestic animals. The compounds of the invention can be administered by any conventional means available for use in conjunction with pharmaceuticals, either as individual therapeutic agents or in a combination of therapeutic agents. The compounds can be administered alone, but are generally administered with a pharmaceutical carrier selected on the basis of the chosen route of administration and standard pharmaceutical practice. The pharmaceutical compositions of the invention may be adapted for oral, parenteral, transdermal, transmucosal, rectal or intranasal administration, and may be in unit dosage form, as is well known to those skilled in the pharmaceutical art. The term "parenteral" as used herein includes subcutaneous, intravenous, intramuscular, or intrasternal injection or infusion techniques.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 10 to 10,000 milligrams per meter$^2$ of body mass (mg/m$^2$), with the preferred dose being 5–5,000 mg/m$^2$ body mass for the oxyalkylene-containing compound, butyric acid, butyric acid salt or butyric acid derivative, and 0.5–10,000 mg/m$^2$ body mass for the β-oxidation inhibitor.

Dosage forms (compositions suitable for administration) contain from about 0.1 mg to about 10 g of active ingredient per unit. In these pharmaceutical compositions the active ingredient(s) will ordinarily be present in an amount of about 0.5–95% by weight based on the total weight of the composition.

The active ingredient(s) can be administered orally in solid or semi-solid dosage forms, such as for example hard or soft-gelatin capsules, tablets, and powders, or in liquid dosage forms, such as elixirs, syrups, disperse powders or granules, emulsions, and aqueous or oily suspensions. It can also be administered parenterally, in sterile liquid dosage forms. Other dosage forms include transdermal administration via a patch mechanism or ointment.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient(s) in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example, maize starch or alginic acid; binding agents, such as starch, gelatin, or acacia; and lubricating agents, for example, magnesium stearate, stearic acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and inert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil, pharmaceutically-accepted synthetic oils and other diluents suitable for the manufacture of capsules. Both tablets and capsules can be manufactured as sustained release-products to provide for continuous release of medication over a period of hours.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acacia; dispersing or wetting agents, such as a naturally occurring phosphatide, e.g., lecithin, or condensation products of an alkylene oxide with fatty acids, for example of polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl or n-propyl p-hydroxy benzoate, one or more coloring agents, one or more flavoring agents, and one or more sweetening agents, such as sucrose, saccharin, or sodium or calcium cyclamate.

Dispersable powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents.

The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, for example, as a solution in 1,3-butanediol.

In general, water, a suitable oil, saline, aqueous dextrose (glucose), polysorbate and related sugar solutions, emulsions, such as Intralipid® (Cutter Laboratories, Inc., Berkley, Calif.) and glycols such as propylene glycol or polyethylene glycols are suitable carriers for parenteral solutions. Antioxidizing agents, such as but not limited to sodium bisulfite, sodium sulfite, or ascorbic acid, either alone or combined, are suitable stabilizing agents. Also used can be citric acid and its salts and sodium EDTA. In addition, parenteral solutions can contain preservatives, such as but not limited to benzalkonium chloride, methyl- or propyl-paraben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan- 2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in *Remington's Pharmaceutical Sciences*, Mack Publishing Company, a standard reference text in this field, which is incorporated herein by reference in its entirety.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

We claim:

1. A method of augmenting the therapeutic activity of an oxyalkylene-containing compound which comprises administering to a patient or host cells an amount of an inhibitor of β-oxidation of fatty acids effective to inhibit the β-oxidation of said the compound, and thereby augment the therapeutic activity of said compound, wherein said compound is represented by the formula:

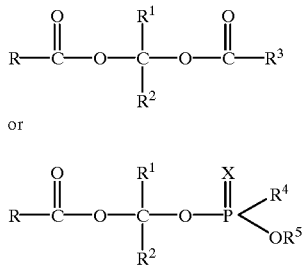

or

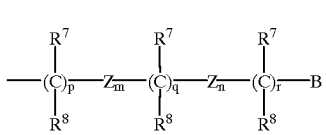

wherein

R is $C_3$ to $C_{10}$ alkyl, $C_3$ to $C_{10}$ alkenyl, $C_3$ to $C_{10}$ alkynyl, aryl, aralkyl, heteroaryl or heteroaralkyl, any of which can be optionally substituted with aryl, heteroaryl, halo, alkyl, alkoxy, hydroxy, amino, cyano, nitro, trifluoromethyl, carbonyl, acylamino, carbamoyl or a combination thereof;

$R^1$ and $R^2$ are independently H, $C_1$ to $C_{10}$ alkyl, $C_2$ to $C_{10}$ alkenyl, or $C_2$ to $C_{10}$ alkynyl, any of which can be optionally substituted with halo, alkoxy, amino, trifluoromethyl, aryl, heteroaryl or a combination thereof;

$R^3$ is
(1) $C_1$ to $C_{10}$ alkyl, $C_2$ to $C_{10}$ alkenyl, $C_2$ to $C_{10}$ alkynyl, aryl, aralkyl, heteroaryl or heteroaralkyl, any of which can be optionally substituted with aryl, heteroaryl, halo, alkyl, alkoxy, hydroxy, amino, cyano, nitro, trifluoromethyl, carbonyl, acylamino, carbamoyl or a combination thereof;
(2) —ACOOR$^6$, wherein A is aryl, heteroaryl, $C_1$ to $C_8$ alkyl, $C_2$ to $C_3$ alkenyl, or $C_2$ to $C_3$ alkynyl, wherein said alkyl, alkenyl or alkynyl is optionally substituted with one or more of hydroxy, halo, lower alkyl, alkoxy, carbonyl, thiol, lower alkylthio, aryl, heteroaryl or combination thereof, and further wherein $R^6$ is H, alkyl, alkenyl, aryl, aralkyl, heteroaryl, heteroaralkyl, or —CR$^1$R$^2$—O—C(O)—R;

(3)

$$-(\underset{R^8}{\overset{R^7}{C}})_p-Z_m-(\underset{R^8}{\overset{R^7}{C}})_q-Z_n-(\underset{R^8}{\overset{R^7}{C}})_r-B$$

wherein Z is —CR$^9$=CR$^{10}$— or —C≡C—; $R^7$, $R^8$, $R^9$ and $R^{10}$ are independently H, alkyl or alkenyl; B is aryl or heteroaryl; m and n are independently integers from 0 to 5; the sum of m and n is from 1 to 5; and p, q and r are independently integers from 0 to 2;

(4) a nitrogen-containing heterocycloalkyl, heterocycloalkenyl, heteroaryl group or heteroaralkyl group, wherein the heteroaryl group and the heteroaralkyl group can have up to two additional substituents;

(5) an aryl or aralkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido, wherein the aryl or aralkyl groups can have up to two additional substituents;

(6) a $C_1$ to $C_{10}$ alkyl, $C_2$ to $C_{10}$ alkenyl, $C_3$ to $C_{10}$ alkynyl or $C_3$ to $C_7$ cycloalkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido;

(7) $C_1$ to $C_{12}$ alkyl or $C_2$ to $C_{10}$ alkenyl substituted with from one to ten substituents selected from the group consisting of hydroxy, alkoxy, acyloxy, aroyloxy and aryloxy, and, optionally having one or more halo groups, wherein adjacent hydroxy groups, if present, can optionally be present as an acetonide;

(8) —$(CH_2)_n$—[O—$(CH_2)_p$]$_m$—$OR^{11}$, —$(CH_2)_n$-PEG-$OR^{11}$, or —$(CH_2)_n$-PPG-$OR^{11}$; wherein $R^{11}$ is $C_1$ to $C_6$ alkyl, $C_2$ to $C_6$ alkenyl, aryl, acyl, aroyl, alkoxycarbonyl, aminocarbonyl or —$(CH_2)_n$—$COOCR^1R^2$—O—C(O)—R; PEG is a polyethylene glycol moiety having an average molecular weight of 200–8000; PPG is a polypropylene glycol moiety having an average molecular weight of 200–8000; p is an integer from 2 to 4; n is an integer from 1 to 5; and m is an integer from 1 to 6;

(9) together with the carbonyl group to which it is attached, an acyl moiety of an inhibitor of β-oxidation of fatty acids ($R^3CO$), wherein said first and second inhibitors are different;

X is oxygen or sulfur;

$R^4$ is independently H, $C_1$ to $C_6$ alkyl, $C_2$ to $C_6$ alkenyl, $C_2$ to $C_6$ alkynyl, aryl, aralkyl, heteroaryl, heteroaralkyl, —$OCR^1R^2$—O—C(O)—R or $OR^5$;

$R^5$ is independently H, $C_1$ to $C_6$ alkyl, $C_2$ to $C_6$ alkenyl, $C_2$ to $C_6$ alkynyl, aryl, aralkyl, heteroaryl, heteroaralkyl or —$CR^1R^2$—O—C(O)—R; or a pharmaceutically-acceptable salt thereof.

2. The method of claim 1 wherein said oxyalkylene-containing compound is pivaloyloxymethyl butyrate or butylidine dibutyrate.

3. The method of claim 1 wherein said oxyalkylene-containing compound is mono-(butyroyloxymethyl) glutarate, bis-(butyroyloxymethyl)glutarate, mono-(1-butyroyloxyethyl)glutarate or bis-(1-butyroyloxyethyl) glutarate.

4. The method of claim 1 wherein said oxyalkylene-containing compound is cinnamoyloxymethyl butyrate, cinnamoyloxymethyl phenylacetate, cinnamoyloxymethyl 4-phenylbutyrate, 1-(cinnamoyl)oxyethyl phenylacetate, 1-(cinnamoyl)oxyethyl 4-phenylbutyrate, 3,4-dimethoxycinnamoyloxymethyl butyrate or 1-(3,4-dimethoxycinnamoyl)oxyethyl butyrate.

5. The method of claim 1 wherein said oxyalkylene-containing compound is 4-(butyramido)butyroyloxymethyl butyrate, 4-(butyramido)benzoyloxymethyl butyrate, 4-aminobenzoyloxymethyl butyrate, 4-aminobenzoyloxymethyl butyrate hydrochloride, 1-(4-aminobenzoyloxy)ethyl butyrate, 3-pyridinecarboxymethyl butyrate, 1-(3-pyridinecarboxy)ethyl butyrate or (N-methylpyridinium)-3-carboxymethyl butyrate chloride.

6. The method of claim 1 wherein said oxyalkylene-containing compound is 2-(2-methoxyethoxy) acetyloxymethyl butyrate, 2-[2-(methoxyethoxy)ethoxy] acetyloxymethyl butyrate, 1-[2-(2-methoxyethoxy)acetyl] oxyethyl butyrate or 1-{2-[2-(2-methoxyethoxy)ethoxy] acetyl}oxyethyl butyrate.

7. The method of claim 1 wherein said oxyalkylene-containing compound is α-methyl-4-(2-methylpropyl)-benzeneacetyloxymethyl butyrate, 1-{α-methyl-4(2-methylpropyl)-benzeneacetyloxy}-ethyl butyrate, 1-{α-methyl-4(2-methylpropyl)-benzeneacetyloxy}-butyl butyrate, 6-methoxy-α-methyl-2-naphthaleneacetyloxylmethyl butyrate, 1-{6-methoxy-α-methyl-2-naphthaleneacetyloxy}-ethyl butyrate or 1-{6-methoxy-α-methyl-2-naphthaleneacetyloxy}-butyl butyrate.

8. The method of claim 1 wherein said oxyalkylene-containing compound is butyroyloxymethyl diethyl phosphate, 1-(1-butyroyloxy)ethyl diethyl phosphate, mono (butyroyloxymethyl)phosphate or 1-{1-(4-phenylbutyroyloxy)ethyl} diethyl phosphate.

9. The method of claim 1 wherein said inhibitor is selected from the group consisting of ketoprofen, diflunisal, salsalate, etodolac, tolmetin, ibuprofen, naproxen, oxaprozin, salicylic acid, acetylsalicylic acid, indomethacin, flurbiprofen, diclofenac, mefenamic acid, meclofenamic acid, ketorolac, sulindac, valproic acid and 2-valproenic acid.

10. The method of claim 1 wherein said therapeutic activity is effective to treat or ameliorate cancer or other proliferative disorder.

11. The method of claim 10 wherein said therapeutic activity is effective to inhibit histone deacetylase in said patient.

12. The method of claim 10 wherein said therapeutic activity is effective to induce cellular apoptosis of cancer cells or proliferating cells of said proliferative disorder.

13. The method of claim 1 wherein said therapeutic activity is effective to cause differentiation of or block proliferation of cancerous or neoplastic cells.

14. The method of claim 1 wherein said therapeutic activity is effective to inhibit telomerase activity in cancer cells and to thereby inhibit malignant progression of said cells.

15. The method of claim 1 which further comprises administering an antiviral agent.

16. The method of claim 15 wherein said further administering is effective to treat or ameliorate a virus-associated tumor selected from the group consisting of an EBV-associated malignancy, Kaposi's sarcoma, an AIDS-related lymphoma, an hepatitis B-associated malignancy and an hepatitis C-associated malignancy.

17. The method of claim 16 wherein said EBV-associated malignancy is nasopharyngeal carcinoma or non-Hodgkin's lymphoma.

18. The method of claim 17 wherein said antiviral agent is ganciclovir, acyclovir, or famciclovir.

19. The method of claim 1 which further comprises administering a pharmaceutical agent to thereby enhance the activity of said agent, wherein said agent is selected from the group consisting of a cytokine, an interleukin, an anti-cancer agent or an anti-neoplastic agent, a chemotherapeutic agent, an antibody, a conjugated antibody, an immune stimulant, an antibiotic, a hormone antagonist or a growth stimulant.

20. The method of claim 19 wherein said antibiotic is selected from the group consisting of ganciclovir, acyclovir, and famciclovir.

21. The method of claim 19 wherein said chemotherapeutic agent is selected from the group consisting of an alkylating agent, a purine analog, a pyrimidine analog, a vinca alkaloid, a vinca-like alkaloid, etoposide, an etoposide-like drug, a corticosteroid, a nitrosourea, an antimetabolite, a platinum-based cytotoxic drug, a hormonal antagonist, an anti-androgen and an anti-estrogen.

22. The method of claim 19 wherein said cytokine is an interferon.

23. The method of claim 19 wherein said immune stimulant is *Corynebacterium parvum* or a sarcolectin.

24. The method of claim 19 wherein the chemotherapeutic agent is selected from the group consisting of tamoxifen, doxorubicin, L-asparaginase, dacarbazine, amascrine, procarbazine, hexamethylmelamine, mitosantrone and gemcitabine.

25. The method of claim 1 which further comprises administering a cytotoxic agent to thereby ameliorate the effects of said cytotoxic agent in a patient by inducing growth arrest of rapidly-proliferating epithelial cells or bone marrow stem cells of said patient.

26. The method of claim 25 wherein said compound is administered simultaneously with, before or after administration of said cytotoxic agent.

27. The method of claim 1 wherein said therapeutic activity is effective to modulate an immune response in said patient.

28. The method of claim 27 wherein modulation of said immune response is effective to enhance cytokine secretion, inhibit or delay apoptosis in polymorphonuclear cells, enhance polymorphonuclear cell function by augmenting hematopoietic growth factor secretion, induce expression of cell surface antigens in tumor cells, enhance progenitor cell recovery after bone marrow transplantation, or a combination thereof.

29. The method of claim 1 wherein said therapeutic activity is effective to increase hemoglobin content in blood of said patient.

30. The method of claim 1 wherein said therapeutic activity is effective to treat a blood disorder in said patient.

31. The method of claim 1 wherein said therapeutic activity is effective to treat a gastrointestinal disorder.

32. The method of claim 1 wherein said therapeutic activity is effective to treat a cutaneous ulcer.

33. The method of claim 1 wherein said therapeutic activity is effective to induce wound healing.

34. The method of claim 1 wherein said therapeutic activity is effective to modulate gene expression in a host or host cells by enhancing, augmenting or repressing expression of a gene of interest.

35. The method of claim 1 wherein said therapeutic activity is effective to enhance insulin expression in an insulin-dependent patient.

36. The method of claim 1 wherein said therapeutic activity is effective to enhance chloride channel expression in a cystic fibrosis patient.

37. The method of claim 1 wherein said therapeutic activity is effective to enhance recombinant gene expression in a recombinant host cell containing an expression system for a butyric acid-responsive gene.

38. The method of claim 37 wherein said host cells are mammalian cells, insect cells, yeast cells or bacterial cells.

39. The method of claim 1 wherein said therapeutic activity is effective to induce tolerance to an antigen.

40. The method of claim 39 wherein said antigen is a self-antigen associated with an autoimmune disease or said antigen is present on a transplanted organ or cells.

41. The method of claim 1 wherein said therapeutic activity is anti-protozoan activity.

42. The method of claim 41 wherein said anti-protozoan activity is anti-malarial, anti-cryptosporidiosis, anti-toxoplasmosis, or anti-coccidiosis activity.

43. The method of claim 41 wherein said anti-protozoan activity is effective to inhibit protozoan histone deacetylase in said patient.

44. The method of claim 1 wherein said therapeutic activity is effective to inhibit histone deacetylase in said host cells.

45. A pharmaceutical composition for augmenting the therapeutic activity of an oxyalkylene-containing compound, butyric acid, a butyric acid salt or a butyric acid derivative which comprises a therapeutically-effective amount of said compound, acid, salt or derivative and an amount of a first inhibitor of β-oxidation of fatty acids effective to inhibit the β-oxidation of said compound, acid, salt or derivative, and thereby augment the therapeutic activity thereof, in admixture with a pharmaceutically acceptable carrier, wherein said oxyalkylene-containing compound is represented by the formula:

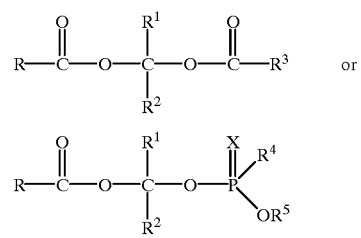

wherein

R is $C_3$ to $C_{10}$ alkyl, $C_3$ to $C_{10}$ alkenyl, $C_3$ to $C_{10}$ alkynyl, aryl, aralkyl, heteroaryl or heteroaralkyl, any of which can be optionally substituted with aryl, heteroaryl, halo, alkyl, alkoxy, hydroxy, amino, cyano, nitro, trifluoromethyl, carbonyl, acylamino, carbamoyl or a combination thereof;

$R^1$ and $R^2$ are independently H, $C_1$ to $C_{10}$ alkyl, $C_2$ to $C_{10}$ alkenyl, or $C_2$ to $C_{10}$ alkynyl, any of which can be optionally substituted with halo, alkoxy, amino, trifluoromethyl, aryl, heteroaryl or a combination thereof;

$R^3$ is (1) $C_1$ to $C_{10}$ alkyl, $C_2$ to $C_{10}$ alkenyl, $C_2$ to $C_{10}$ alkynyl, aryl, aralkyl, heteroaryl or heteroaralkyl, any of which can be optionally substituted with aryl, heteroaryl, halo, alkyl, alkoxy, hydroxy, amino, cyano, nitro, trifluoromethyl, carbonyl, acylamino, carbamoyl or a combination thereof;

(2) —ACOOR$^6$, wherein A is aryl, heteroaryl, $C_1$ to $C_8$ alkyl, $C_2$ to $C_3$ alkenyl, or $C_2$ to $C_3$ alkynyl, wherein said alkyl, alkenyl or alkynyl is optionally substituted with one or more of hydroxy, halo, lower alkyl, alkoxy, carbonyl, thiol, lower alkylthio, aryl, heteroaryl or combination thereof, and further wherein $R^6$ is H, alkyl, alkenyl, aryl, aralkyl, heteroaryl, heteroaralkyl, or —CR$^1$R$^2$—O—C(O)—R;

(3)

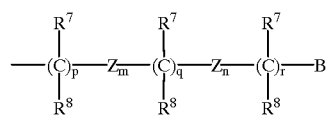

wherein Z is —CR$^9$=CR$^{10}$— or —C≡C—; $R^7$, $R^8$, $R^9$ and $R^{10}$ are independently H, alkyl or alkenyl; B is aryl or heteroaryl; m and n are independently integers from 0 to 5; the sum of m and n is from 1 to 5; and p, q and r are independently integers from 0 to 2;

(4) a nitrogen-containing heterocycloalkyl, heterocycloalkenyl, heteroaryl group or heteroaralkyl group, wherein the heteroaryl group and the heteroaralkyl group can have up to two additional substituents;

(5) an aryl or aralkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido, wherein the aryl or aralkyl groups can have up to two additional substituents;

(6) a $C_1$ to $C_{10}$ alkyl, $C_2$ to $C_{10}$ alkenyl, $C_3$ to $C_{10}$ alkynyl or $C_3$ to $C_7$ cycloalkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido;

(7) $C_1$ to $C_{12}$ alkyl or $C_2$ to $C_{10}$ alkenyl substituted with from one to ten substituents selected from the group consisting of hydroxy, alkoxy, acyloxy, aroyloxy and aryloxy, and, optionally having one or more halo groups, wherein adjacent hydroxy groups, if present, can optionally be present as an acetonide;

(8) —$(CH_2)_n$—[O—$(CH_2)_p$]$_m$—$OR^{11}$, —$(CH_2)_n$-PEG-$OH^{11}$, or —$(CH_2)_n$-PPG-$OR^{11}$; wherein $R^{11}$ is $C_1$ to $C_6$ alkyl, $C_2$ to $C_6$ alkenyl, aryl, acyl, aroyl, alkoxycarbonyl, aminocarbonyl or —$(CH_2)_n$—$COOCR^1R^2$—O—C(O)—R; PEG is a polyethylene glycol moiety having an average molecular weight of 200–8000; PPG is a polypropylene glycol moiety having an average molecular weight of 200–8000; p is an integer from 2 to 4; n is an integer from 1 to 5; and m is an integer from 1 to 6;

(9) together with the carbonyl group to which it is attached, an acyl moiety of an inhibitor of β-oxidation of fatty acids ($R^3CO$), wherein said first and second inhibitors are different;

X is oxygen or sulfur;

$R^4$ is independently H, $C_1$ to $C_6$ alkyl, $C_2$ to $C_6$ alkenyl, $C_2$ to $C_6$ alkynyl, aryl, aralkyl, heteroaryl, heteroaralkyl, —$OCR^1R^2$—O—C(O)—R or $OR^5$;

$R^5$ is independently H, $C_1$ to $C_6$ alkyl, $C_2$ to $C_6$ alkenyl, $C_2$ to $C_6$ alkynyl, aryl, aralkyl, heteroaryl, heteroaralkyl or —$CR^1R^2$—O—C(O)—R; or a pharmaceutically-acceptable salt thereof.

46. The composition of claim 45 wherein said oxyalkylene-containing compound is pivaloyloxymethyl butyrate or butylidine dibutyrate.

47. The composition of claim 45 wherein said oxyalkylene-containing compound is mono (butyroyloxymethyl)glutarate, bis-(butyroyloxymethyl) glutarate, mono-(1-butyroyloxyethyl)glutarate or bis-(1-butyroyloxyethyl)glutarate.

48. The composition of claim 45 wherein said oxyalkylene-containing compound is cinnamoyloxymethyl butyrate, cinnamoyloxymethyl phenylacetate, cinnamoyloxymethyl 4-phenylbutyrate, 1-(cinnamoyl)oxyethyl phenylacetate, 1-(cinnamoyl)oxyethyl 4-phenylbutyrate, 3,4-dimethoxycinnamoyloxymethyl butyrate or 1-(3,4-dimethoxycinnamoyl)oxyethyl butyrate.

49. The composition of claim 45 wherein said oxyalkylene-containing compound is 4-(butyramido) butyroyloxymethyl butyrate, 4-(butyramido) benzoyloxymethyl butyrate, 4-aminobenzoyloxymethyl butyrate, 4-aminobenzoyloxymethyl butyrate hydrochloride, 1-(4-aminobenzoyloxy)ethyl butyrate, 3-pyridinecarboxymethyl butyrate, 1-(3-pyridinecarboxy) ethyl butyrate or (N-methylpyridinium)-3-carboxymethyl butyrate chloride.

50. The composition of claim 45 wherein said oxyalkylene-containing compound is 2-(2-methoxyethoxy) acetyloxymethyl butyrate, 2-[2-(methoxyethoxy)ethoxy] acetyloxymethyl butyrate, 1-[2-(2-methoxyethoxy)acetyl] oxyethyl butyrate or 1-{2-[2-(2-methoxyethoxy)ethoxy] acetyl}oxyethyl butyrate.

51. The composition of claim 45 wherein said oxyalkylene-containing compound is α-methyl-4-(2-methylpropyl)-benzeneacetyloxymethyl butyrate, 1-{α-methyl-4(2-methylpropyl)-benzeneacetyloxy}-ethyl butyrate, 1-{α-methyl-4(2-methylpropyl)-benzeneacetyloxy}-butyl butyrate, 6-methoxy-α-methyl-2-naphthaleneacetyloxylmethyl butyrate, 1-{6-methoxy-α-methyl-2-naphthaleneacetyloxy}-ethyl butyrate or 1-{6-methoxy-α-methyl-2-naphthaleneacetyloxy}-butyl butyrate.

52. The composition of claim 45 wherein said oxyalkylene-containing compound is butyroyloxymethyl diethyl phosphate, 1-(1-butyroyloxy)ethyl diethyl phosphate, mono(butyroyloxymethyl) phosphate or 1-{1-(4-phenylbutyroyloxy)ethyl} diethyl phosphate.

53. The composition of claim 45 wherein said derivative is isobutyramide, monobutyrin, tributyrin, 2-phenylbutyric acid, 3-phenylbutyric acid, 4-phenylbutyric acid, phenylacetic acid, cinnamic acid, α-methyldihydrocinnamic acid, 3-chloropropionic acid or vinylacetic acid.

54. The composition of claim 45 wherein said butyric acid salt is a sodium, arginine or lysine salt.

55. The composition of claim 45 wherein said butyric acid salt is arginine butyrate.

56. The composition of claim 45 wherein said inhibitor is selected from the group consisting of ketoprofen, diflunisal, salsalate, etodolac, tolmetin, ibuprofen, naproxen, oxaprozin, salicylic acid, acetylsalicylic acid, indomethacin, flurbiprofen, diclofenac, mefenamic acid, meclofenamic acid, ketorolac, sulindac, valproic acid and 2-valproenic acid.

57. The composition of claim 45 which further comprises a pharmaceutical agent selected from the group consisting of a cytokine, an interleukin, an anti-cancer agent, a chemotherapeutic agent, an antibody, a conjugated antibody, an immune stimulant, an antibiotic, a hormone antagonist, a growth stimulant, an antiviral agent and a cytotoxic agent.

58. The composition of claim 57 wherein said antiviral agent is ganciclovir, acyclovir, or famciclovir.

59. The composition of claim 57 wherein said chemotherapeutic agent is selected from the group consisting of an alkylating agent, a purine analog, a pyrimidine analog, a vinca alkaloid, a vinca-like alkaloid, etoposide, an etoposide-like drug, a corticosteroid, a nitrosourea, an antimetabolite, a platinum-based cytotoxic drug, a hormonal antagonist, an anti-androgen and an anti-estrogen.

60. The composition of claim 57 wherein said cytokine is an interferon.

61. The composition of claim 57 wherein said immune stimulant is *Corynebacterium parvum* or a sarcolectin.

62. The composition of claim 57 wherein the chemotherapeutic agent is selected from the group consisting of tamoxifen, doxorubicin, L-asparaginase, dacarbazine, amascrine, procarbazine, hexamethylmelamine, mitosantrone and gemcitabine.

63. The composition of claim 57 wherein said cytotoxic agent induces growth arrest of rapidly-proliferating epithelial cells or bone marrow stem cells of said patient.

* * * * *

UNITED STATES PATENT AND TRADEMARK OFFICE
CERTIFICATE OF CORRECTION

PATENT NO. : 5,939,455
DATED : August 17, 1999
INVENTOR(S) : Ada Rephaeli

It is certified that error appears in the above-indentified patent and that said Letters Patent is hereby corrected as shown below:

Column 4, line 59, after "effective to" delete "provide";

Column 6, line 10, after "non-Hodgkins'" delete "0";

Column 7, line 8, before "method" insert -- the --;

Column 8, line 4, after "can be used to" delete "to" (second occurrence);

Column 8, line 5, change "ameliorating" to -- ameliorate --;

Column 13, line 15, change "supports" to -- support --;

Column 13, line 28, after "mice can be injected" delete "injected" (second occurrence); and Column 16, line 53, after "or" delete "a".

Signed and Sealed this

Tenth Day of April, 2001

Attest:

NICHOLAS P. GODICI

Attesting Officer

Acting Director of the United States Patent and Trademark Office